United States Patent
Walter et al.

(10) Patent No.: US 8,687,858 B2
(45) Date of Patent: Apr. 1, 2014

(54) METHOD AND DEVICE FOR PRODUCING THIN SECTIONS OF A SAMPLE BY MEANS OF AN IMAGE RECOGNITION SYSTEM

(75) Inventors: Roland Walter, Reilingen (DE);
Andreas Laudat, Meckesheim (DE);
Annett Leonhardt, Meckesheim (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 1242 days.

(21) Appl. No.: 12/537,561

(22) Filed: Aug. 7, 2009

(65) Prior Publication Data
US 2010/0118133 A1    May 13, 2010

(30) Foreign Application Priority Data
Aug. 8, 2008 (DE) .................. 10 2008 037 149
May 20, 2009 (DE) .................. 10 2009 022 157

(51) Int. Cl.
*G06K 9/00* (2006.01)

(52) U.S. Cl.
USPC .............. 382/128; 348/79; 435/40.52; 83/13; 83/74; 702/170

(58) Field of Classification Search
None
See application file for complete search history.

(56) References Cited

U.S. PATENT DOCUMENTS

| | | | | |
|---|---|---|---|---|
| 5,226,335 A * | 7/1993 | Sitte et al. | ........................ | 83/74 |
| 5,546,323 A * | 8/1996 | Bacus et al. | .................. | 702/170 |
| 5,974,167 A | 10/1999 | Reszler | | |
| 6,330,348 B1 * | 12/2001 | Kerschmann et al. | ........ | 382/128 |
| 7,374,907 B1 * | 5/2008 | Voneiff et al. | ............. | 435/40.52 |
| 2007/0053057 A1 | 3/2007 | Zust et al. | | |
| 2007/0199418 A1 * | 8/2007 | Ito | ................................... | 83/13 |

FOREIGN PATENT DOCUMENTS

| | | |
|---|---|---|
| EP | 0 592 997 | 4/1994 |
| WO | 9802851 | 1/1998 |
| WO | 9900767 | 1/1999 |
| WO | 0042897 | 7/2000 |
| WO | 0062035 | 10/2000 |

OTHER PUBLICATIONS

Combined Search and Examination Report; GB0913463.6; UK Intellectual Property Office; Oct. 28, 2009.

* cited by examiner

*Primary Examiner* — Sath V Perungavoor
*Assistant Examiner* — Dakshesh Parikh
(74) *Attorney, Agent, or Firm* — Schlee IP International, P.C.; Alexander R. Schlee

(57) ABSTRACT

A method and a device for producing thin sections of a sample by means of a microtome is described, in which a camera acquires at least one image of a surface generated by sectioning of the sample. With the aid of an evaluation device, the image of the surface is evaluated in terms of predefined characteristic values of a section quality. As a function of the characteristic values that are identified, a decision is then made as to whether the section of the sample is accepted or not.

14 Claims, 9 Drawing Sheets

METHOD AND DEVICE FOR PRODUCING THIN SECTIONS OF A SAMPLE BY MEANS OF AN IMAGE RECOGNITION SYSTEM

CROSS-REFERENCE TO RELATED APPLICATION

This application claims the priority of the German patent applications DE 102008037149.1 having a filing date of Aug. 8, 2008 and DE 102009022157.3 having a filing date of May 20, 2009, the entire content of both prior German patent applications being herewith incorporated by reference.

BACKGROUND OF THE INVENTION

The invention relates to a method and a device for producing thin sections of a sample by means of a microtome.

The thin sections produced by the microtome are usually examined carefully by a user and checked as to whether they meet certain quality criteria so that upon subsequent microscopy, the information content in the respective thin section can be evaluated. With such a procedure, it is necessary for the user to possess special knowledge and experience in the field of the production of thin sections and in the field of microscopy, in order to obtain maximum information recovery from the sample, e.g. a body tissue sample. For example, thin sections of a sample embedded in paraffin should be produced only at points where the sample has been precut sufficiently deeply, and where a relatively large cross-sectional surface of it can be investigated. The thin sections should contain no, or only a few, longitudinal grooves and/or transverse grooves, which can result in misinterpretation under the microscope. In addition, the thickness of the thin section must fluctuate only within permissible tolerance limits. When a large number of samples must be investigated, the work necessary for assessment of the quality criteria of thin sections is fatiguing for the user, and incorrect evaluations can occur.

WO00/62035 A1 discloses a system and a method for automatic processing of tissue samples. With the aid of an optical image-producing system, the location of a tissue sample within a paraffin can be determined, and the tissue sample to be sectioned can be aligned. In addition, an optical image-producing method can be used to assist the placement of thin sections onto specimen slides.

SUMMARY OF THE INVENTION

It is an object of the invention to describe a method for producing thin sections of a sample by means of a microtome, and a device for carrying out the method, with which high quality is guaranteed for the thin sections that are produced.

This object is achieved by a method for producing thin sections of a sample by means of a microtome, comprising the method steps of: acquiring at least one image of a surface generated by sectioning of the sample by means of a camera, evaluating the image of the surface in terms of predefined characteristic values of a section quality by means of an evaluation device, and based on a function of the characteristic values that are identified, deciding whether the section of the sample is accepted or not accepted.

According to the invention, a camera acquires at least one image of a surface generated by sectioning of the sample. An evaluation device evaluates the image of the surface in terms of predefined characteristic values of a section quality. As a function of the characteristic values that are identified, a decision is then made as to whether the section of the sample is accepted or not accepted.

The use of a camera, and of an evaluation device that evaluates the image acquired by the camera, objectivizes the assessment operation for the section of the sample. This section of the sample can be a thin section that is later to be investigated by microscopy, or can be an initial cut into the sample to locate a trimming plane (as will be described in further detail below) proceeding from which thin sections are produced. With the aid of the evaluation device and predetermined characteristic values of a section quality, a decision is made as to whether the section of the sample is accepted or not accepted. Because this decision is made on the basis of objectivizable characteristic values, the result is excellent reproducibility of results for the method according to the invention, along with high assessment quality.

The evaluation device preferably encompasses an image processing program that identifies a variety of characteristic values. Image processing programs of this kind can identify outlines of the sample material by evaluating a light/dark contrast, and calculate therefrom the cross-sectional area of the sectioned sample. It is likewise possible, with the aid of an image processing program of this kind and a contrast evaluation system, to detect longitudinal striations and/or transverse striations, to sense their dimensional extensions or other irregularities in the image of the sectioned sample, and to calculate associated characteristic quantities.

It is advantageous if the user, in a teach-in phase, informs the evaluation device, in communication with the evaluation device (e.g. by pressing keys), as to which images of the sample or which thin sections are acceptable after manual inspection, and which are not acceptable. The image processing program then identifies, based on the associated images, characteristic values that can be allocated to the acceptable sections or unacceptable sections. For example, the image processing program examines all images of the sections judged to be "good" for common features and patterns, and identifies the value range of the characteristic values in accordance with different quality criteria. It is thereby possible to inform the evaluation device objectively, in the teach-in phase, as to which acquired sections are acceptable. The procedure is the same with the unacceptable sections, so that after the teach-in phase is concluded, the evaluation device can determine on the basis of a current section whether it is a section judged to be "good" or a section judged to be "poor." The various characteristic values identified by the image processing program are stored in a database. When a sufficiently large data inventory exists, the user can leave further evaluation of new sections entirely to the evaluation device. The user also has the capability, however, of continuing to assess section quality manually and of being assisted, by way of an indication of the result of the evaluation by the evaluation device, in his or her decision regarding acceptable sections or unacceptable sections. If the user determines, after an extended test phase, that the evaluation device is operating in satisfactory fashion in assessing section quality, he or she can switch over to an automatic operating mode in which the section cutting action and the assessment of the quality of the sections that have been cut out are carried out automatically with no intervention by the user.

The quality demands in terms of thin-section quality or the section image may deviate greatly from one another in different areas of utilization. With the aid of the teach-in phase described above, objective assessment criteria that enable semiautomatic operation or indeed fully automatic operation can be identified even for differing applications.

According to a further aspect of the invention, a device for carrying out the method described is indicated.

BRIEF DESCRIPTION OF THE DRAWINGS

Exemplifying embodiments of the invention are described hereinafter with reference to the Figures, in which.

DETAILED DESCRIPTION OF THE DRAWINGS

Figure 1:
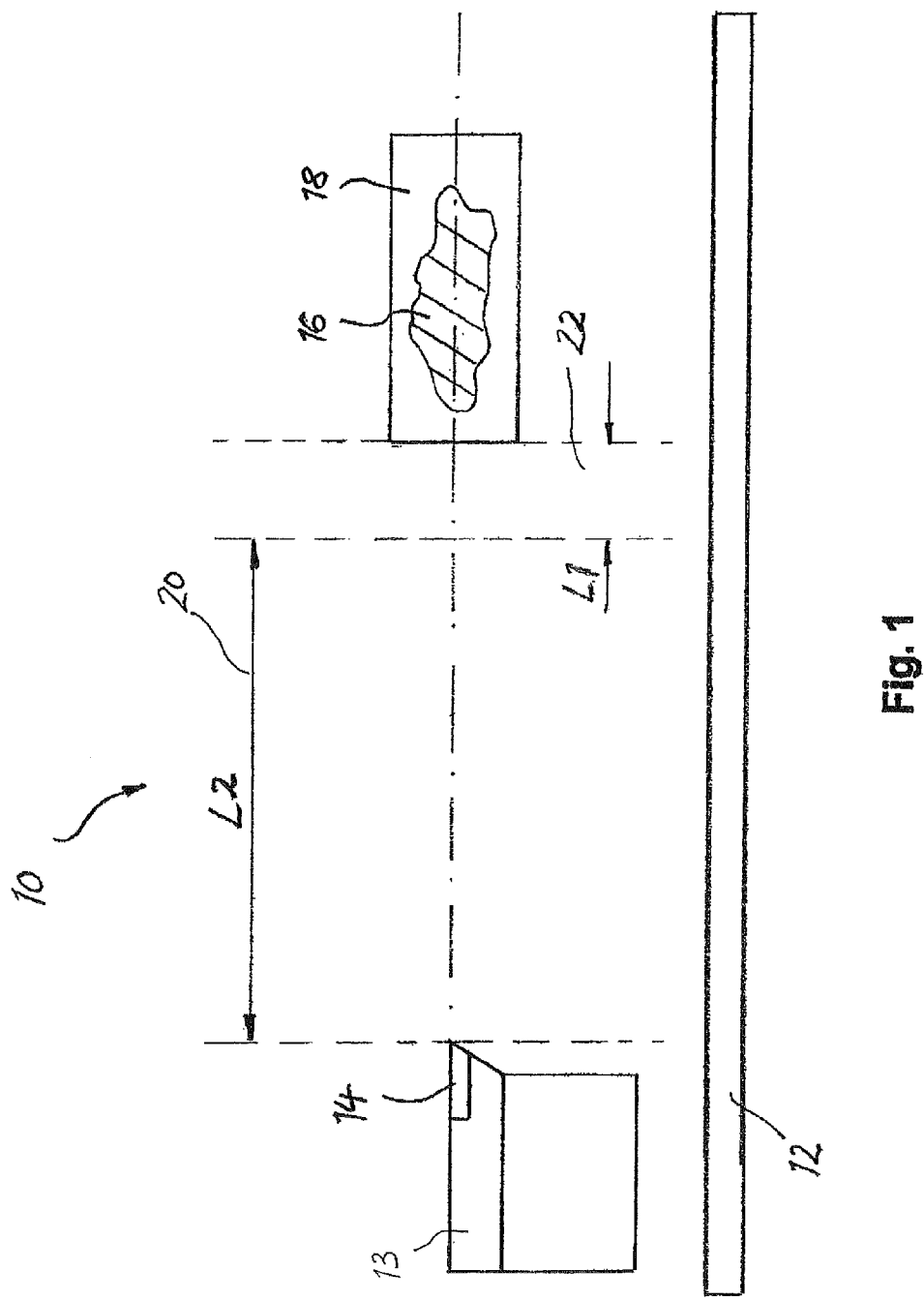
FIG. 1 is a side view of a microtome with a sample to be split.

FIG. 1 is a simplified depiction, in a side view, of a microtome 10 having a base bed 12, a sectioning knife holder 13 that holds a sectioning knife 14, and a sample 16 that is embedded in a paraffin block 18 and from which thin sections of sufficiently high section quality for microscopy are to be produced largely automatically. During the operation of microtome 10, firstly, in a coarse drive setting, sectioning knife 14 is quickly brought close to paraffin block 18 in which sample 16 is embedded, sectioning knife 14 being moved to a location at which a close-in region 22, adjacent to paraffin block 18 and having a length L1, is defined. In this coarse drive mode, sectioning knife 14 travels over a displacement path 20 having a length L2 that is much greater than length L1 of close-in region 22. When sectioning knife 14 goes beyond close-in region 22 that is monitored by a sensor (not depicted in FIG. 1), an automatic sectioning process begins, initially in trimming mode in order to look for a trimming plane, the section thickness for sectioning in trimming mode being in the range from 10 to 50 µm, preferably in the range from 20 to 30 µm. Once the trimming plane has been identified, the sectioning process is then continued in a thin-section mode in order to produce thin sections, the section thickness for sectioning in thin-section mode being in the range from 1 to 10 µm, by preference in the range from 2 to 5 µm, and the sectioning process occurring at a reduced sectioning speed as compared with the trimming mode. The automatic sectioning process is explained in further detail with reference to FIGS. 2 and 3.

Figure 2:
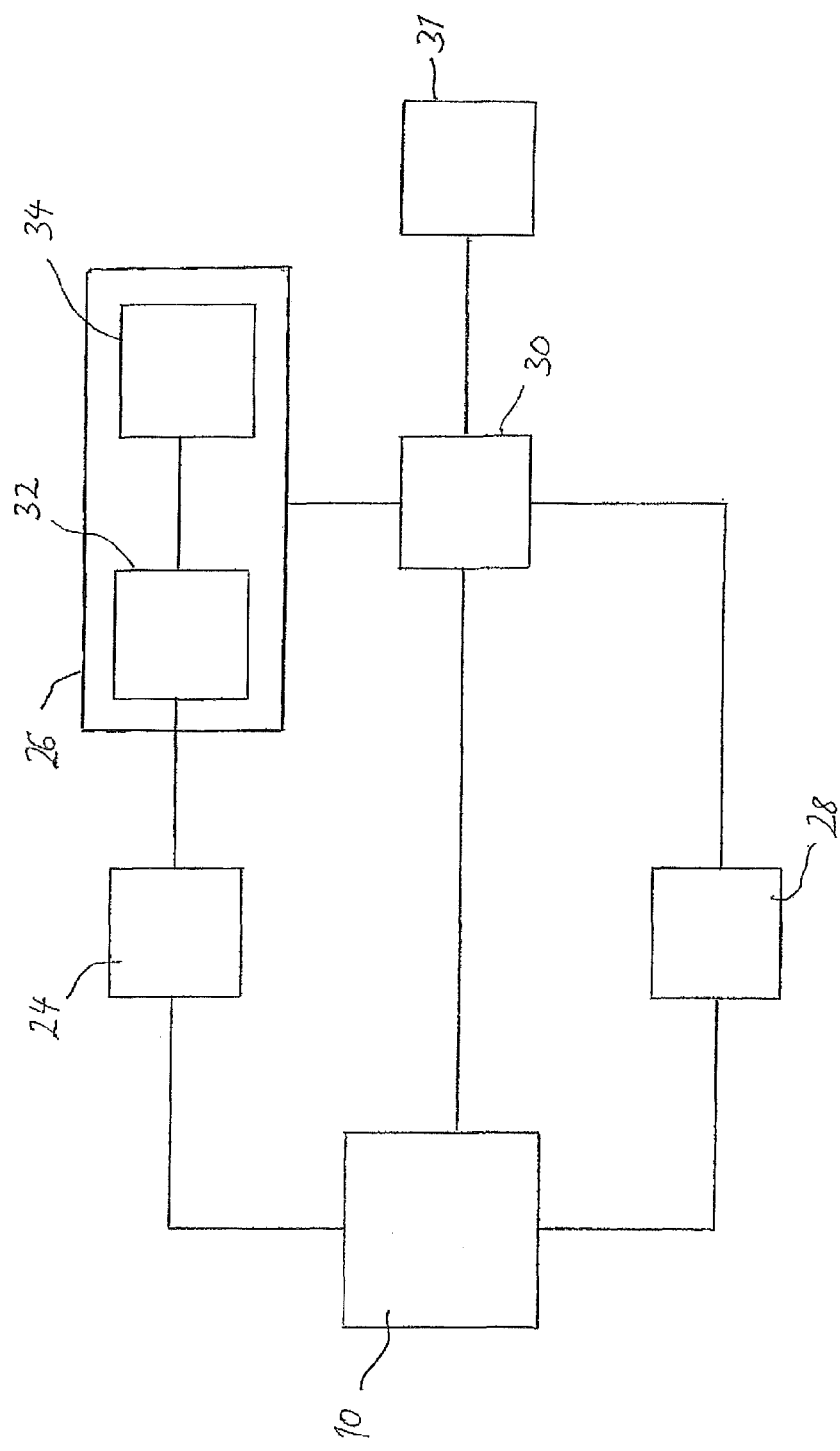
FIG. 2 schematically depicts the hardware configuration of a device for automatically producing thin sections.

FIG. 2 schematically depicts the hardware configuration of a device for automatically producing thin sections. The fully automated microtome 10 is connected to an operating console 28 and to a camera 24 that is coupled to an evaluation device 26, and to a central control unit 30 and a display apparatus 31. Evaluation device 26 and operating console 28 are in turn connected to central control unit 30, evaluation device 26 encompassing a data acquisition system 32 and an image processing program 34. Upon manual actuation of a start/stop button on operating console 28, an operator can trigger a start signal in central control unit 30, so that microtome 10 is switched on and the automatic sectioning process can begin. The sectioning process can also be ended prematurely by once again actuating the start/stop button on operating console 28.

Figure 3:
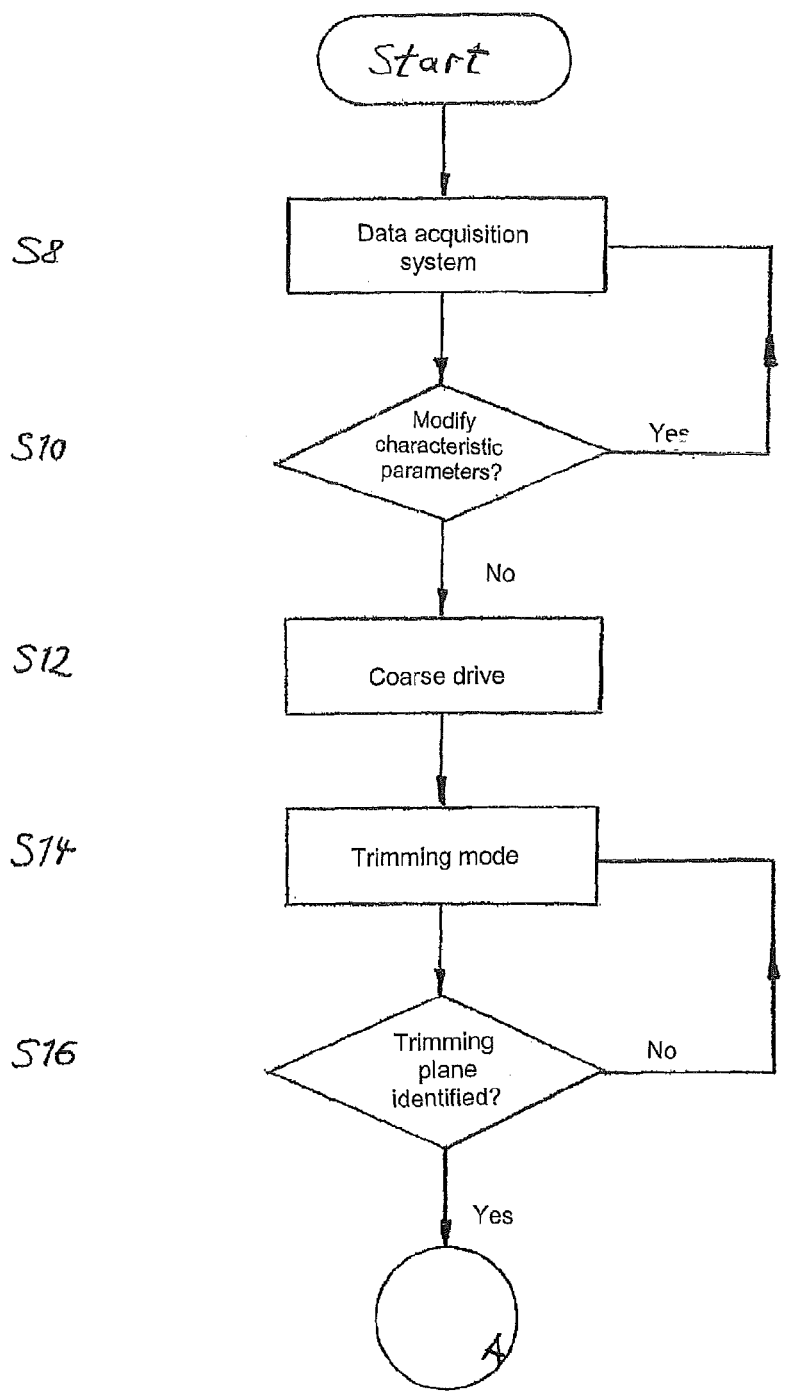
FIG. 3 is a flow chart of execution of the method for automatically producing thin sections.
Figure 3A:
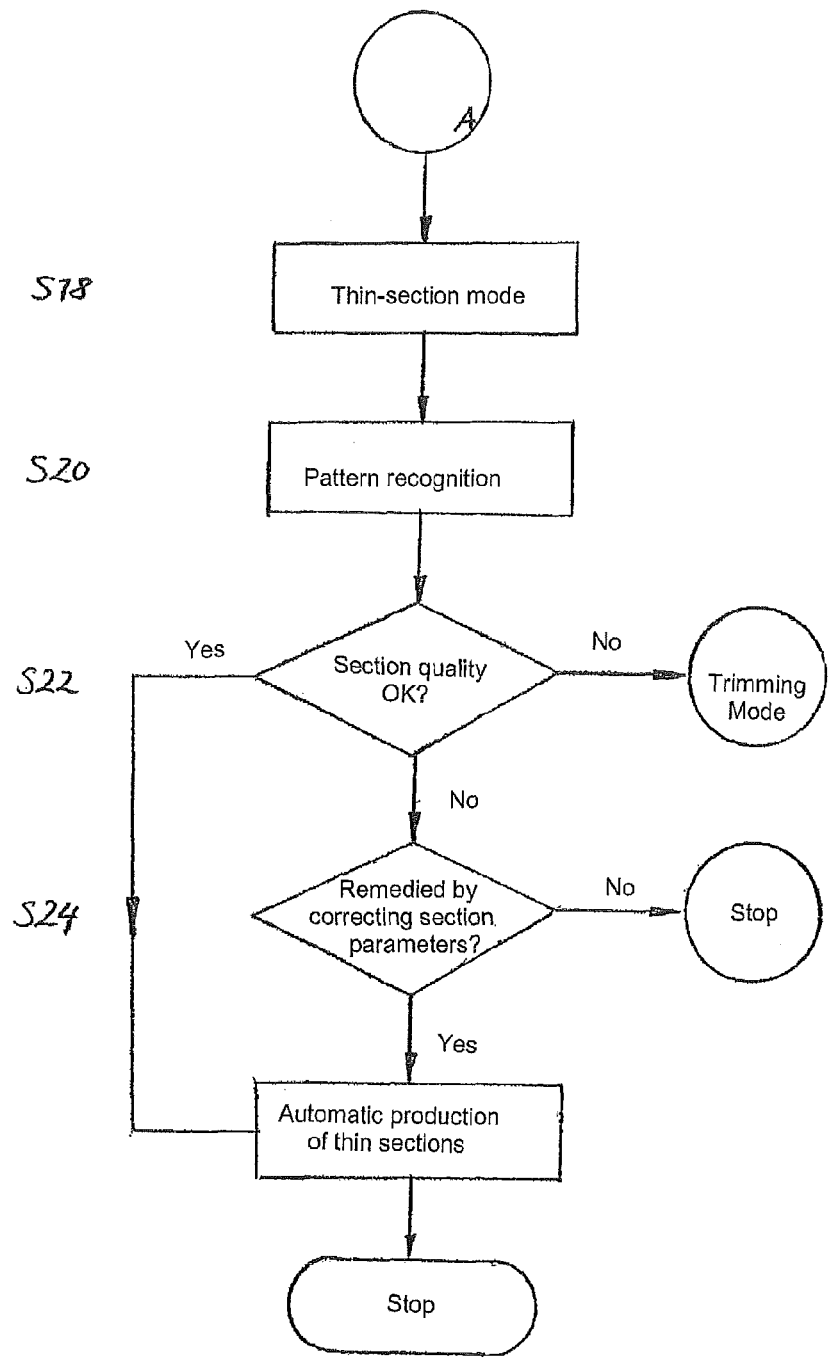
FIG. 3A is a flow chart of execution of the method for automatically producing thin sections.

FIG. 3 and FIG. 3A is a flow chart regarding execution of a method for automatically producing thin sections of a sample 16 using microtome 10. In a teach-in phase, in first step S8 a data set in data acquisition system 32 having characteristic values for the quality of the thin sections is firstly predefined by a user. In this teach-in phase, images of the surface generated by the sectioning of sample 16 are acquired with the aid of camera 24 for a defined number of thin sections, the section quality of the thin sections being subdivided by the user, subjectively, into the category of "good" or "poor." With the aid of image processing program 34, the images acquired of the thin sections accepted and not accepted by the user are then examined in terms of the characteristic values for thin-section quality, in order to identify the associated limit values for those characteristic values for sufficiently good section quality.

Thick-thin effects are, for example, one characteristic value for thin-section quality. With such thick-thin effects, thick and thin sections occur alternately during the sectioning process; the variation in section thickness for an acceptable thin section in thin-section mode should be no more than ±0.2 µm. Another characteristic value for thin-section quality is the number and width of longitudinal striations and/or transverse grooves on the sectioned area of sample 16; the respective maximum permissible number of longitudinal striations or transverse grooves should be five, and the width of the longitudinal striations or transverse grooves for acceptable thin sections should be no greater than 0.5 µm. The user of microtome 10 has the capability of modifying the predefined characteristic values for thin-section quality if necessary. Various characteristic values for thin-section quality are explained in further detail below with reference to FIGS. 13 to 15.

Data acquisition system 32 thus contains, in the teach-in phase, data as to which limit values must not be exceeded by the characteristic values for thin-section quality so that the thin section of sample 16 to be sectioned is still accepted. For better identification of individual tissue types, all the samples 16 that are to be investigated are coded with serial numbers. The code additionally contains information as to the procedure to be used for sample 16, and as to the size of the maximum cross-sectional area of the individual samples 16 in the section direction.

In the second step S10 of the method, a query is made as to whether the stored characteristic values for thin-section quality are to be modified by the user. After any modification, or after confirmation of the characteristic values, in step S12 provision is made for quickly bringing sectioning knife 14 close to sample 16 in the coarse drive setting. The sectioning process then begins in the next step S14, firstly in trimming mode with an advance of approximately 20 to 30 μm per trimming cut, in order to identify the trimming plane.

A suitable trimming plane is understood as that sectioned plane of the sectioned sample 16 which is suitable for continuing the sectioning process in thin-section mode with an advance of approximately 2 to 5 μm in order to produce thin sections. The suitable trimming plane is identified when, as a result of the sectioning process on paraffin block 18 in which sample 16 is embedded, the sectioned area of the initially cut sample 16 is of approximately the same size as the maximum cross-sectional area of sample 16 in the section direction. Identification of the trimming plane in trimming mode is explained in further detail with reference to FIGS. 4 to 12.

A switchover between the trimming mode and thin-section mode occurs only when a trimming depth is reached at which the sectioned area of sample 16 is equal to at least 80% of its maximum cross-sectional area, since it is only at this trimming depth that sample 16 is considered sufficiently precut. In thin-section mode, the sectioning process is then continued in the next step S18, using a sectioning speed reduced as compared with the trimming mode and with a decreased advance, to produce thin sections.

In order to assess section quality, at each sectioning operation to produce a thin section, an image of the surface generated by the sectioning of sample 16 is automatically acquired with the aid of camera 24. Evaluation device 26, which is connected to camera 24, serves not only for determination of the trimming plane, but also for the detection and evaluation of specific patterns in the image, in particular for evaluation of the image in terms of defined characteristic values for thin-section quality.

In the next step S20, a comparison is then made between the specific patterns of the image and the characteristic values for thin-section quality stored in data acquisition system 32, evaluation device 26 being able to assess the section quality of the sample's sectioned area as either "good" or "poor." Evaluation device 26 categorizes section quality as "poor," for example, if the number of longitudinal striations is greater than five. If section quality is categorized as "good," the next sectioning operation continues to be performed in thin-section mode. If section quality after several sectioning operations is categorized as "poor," for example because the number of longitudinal striations on the sample's sectioned area is too high, the next sectioning operation is then performed not in thin-section mode, but rather in trimming mode in order to determine a new trimming plane.

If section quality after a sectioning operation is categorized as "good," then in step S22 a signal is triggered in central control unit 30 so that the sectioning process can occur in thin-section mode in order to produce thin sections.

If section quality is not categorized as "good" after several sectioning operations, then in the last step S24 an automatic correction is made of sectioning parameters such as, for example, the sectioning speed, section thickness, and relief angle, the automatic correction being dependent on the characteristic values identified for thin-section quality. If crumpling of the section is excessive, for example, a decrease in sectioning speed or a readjustment of the relief angle is necessary. For thick-thin effects, a correction in the setting for section thickness is required.

A further important action in order to improve the section quality of the thin sections can be a replacement of sectioning knife 14. For example, if the predetermined maximum permissible number of longitudinal striations or transverse grooves on the sectioned area of sample 16 is exceeded, a replacement of sectioning knife 14 is performed.

If section quality is not improved even after correction of the sectioning parameters, the user then receives a notification that thin sections cannot be produced from sample 16 that is to be sectioned, and that reprocessing of sample 16, for example in the form of additional demineralization, is necessary. This purpose is served by display apparatus 31, which indicates to the user whether the current thin section is accepted or not accepted.

The method for automatic identification of the suitable trimming plane is explained in further detail with reference to FIGS. 4 to 12. This trimming plane is identified when the sectioned area of sample 16 is equal to at least 80% of its maximum cross-sectional area, the identification of which is described below. The associated depth is referred to as the relative trimming depth. The relative trimming depth is thus an indication of the extent to which section 16 is precut. For example, the relative trimming depth is equal to 100% when the area of the precut sample 16 is equal to the maximum cross-sectional area of sample 16 in the section direction. If sample 16 embedded in paraffin block 18 is uncut, the trimming depth is 0%. The relative trimming depth can be identified by the fact that after each sectioning operation in trimming mode, camera 24 acquires at least one image of the surface of paraffin block 18 in which sample 16 is embedded. This image is investigated, with the aid of evaluation device 26, in terms of a contrast difference between the bright surface of paraffin 18 and the dark or non-glossy sectioned area of the precut sample 16. By way of this contrast difference it is possible to determine the size of the sectioned area of the precut sample 16, from which the relative trimming depth can in turn be identified by calculating the ratio between the sectioned area of the precut sample 16 and the maximum cross-sectional area of sample 16 in the section direction.

Figure 4:
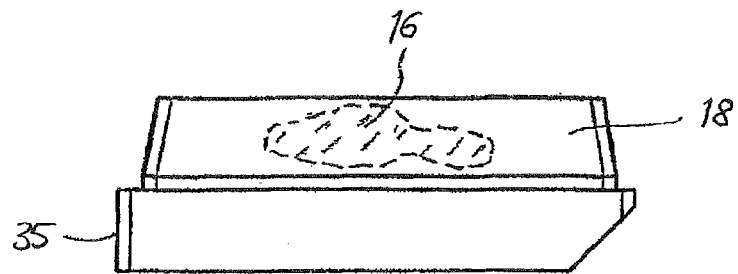
FIG. 4 is a side view of a cassette having a paraffin block and a sample arranged therein.
Figure 5:
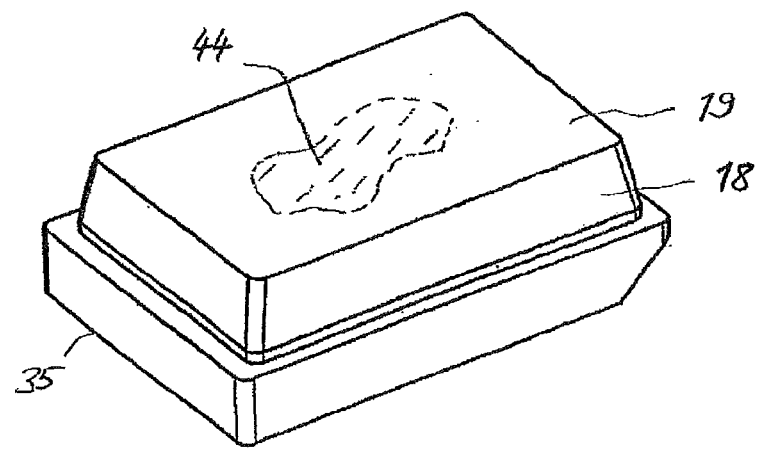
FIG. 5 is a perspective view of the arrangement according to FIG. 4.
Figure 6:
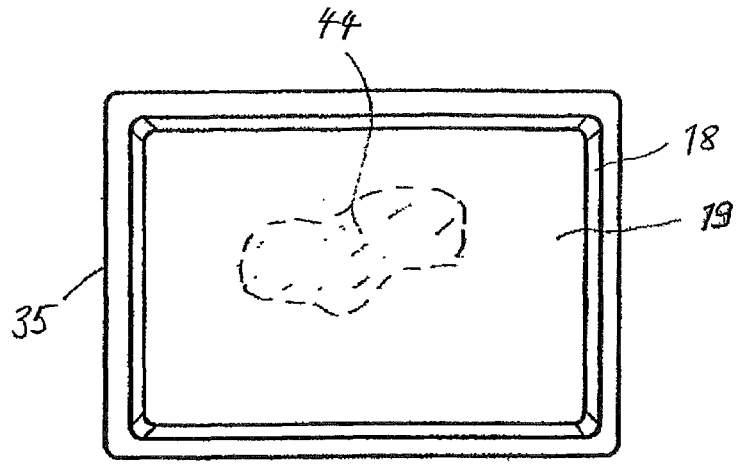
FIG. 6 is a plan view of the arrangement according to FIG. 4.

FIGS. 4 to 6 depict, from various perspectives, paraffin block 18 in which sample 16 to be sectioned is embedded, paraffin block 18 being arranged on a cassette 35. In this case the previously defined relative trimming depth is 0%, since sample 16 has not been precut.

FIGS. 7 to 9 depict, once again from various perspectives, paraffin block 18 in which a precut sample 16 is embedded, sectioned area 17 of the precut sample 16 being equal to approximately 25% of maximum cross-sectional area 44 of sample 16 in the section direction. In this case the relative trimming depth is 25%.

Figure 7:
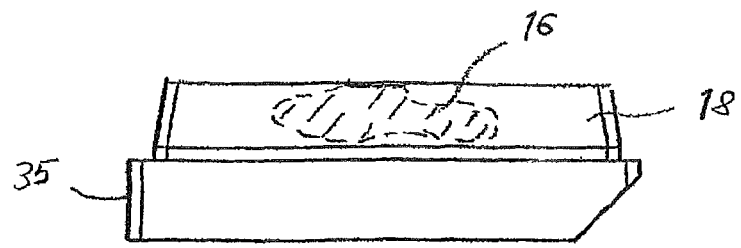
FIG. 7 shows the arrangement according to FIG. 4 with a precut sample.
Figure 8:
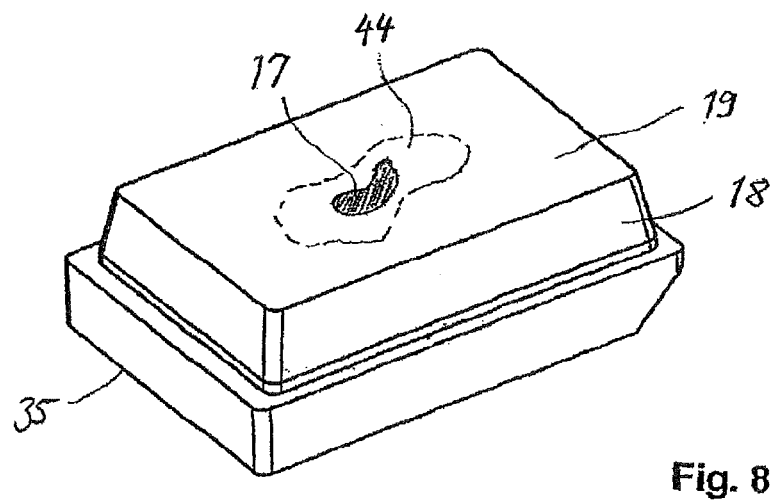
FIG. 8 is a perspective view thereof.
Figure 9:
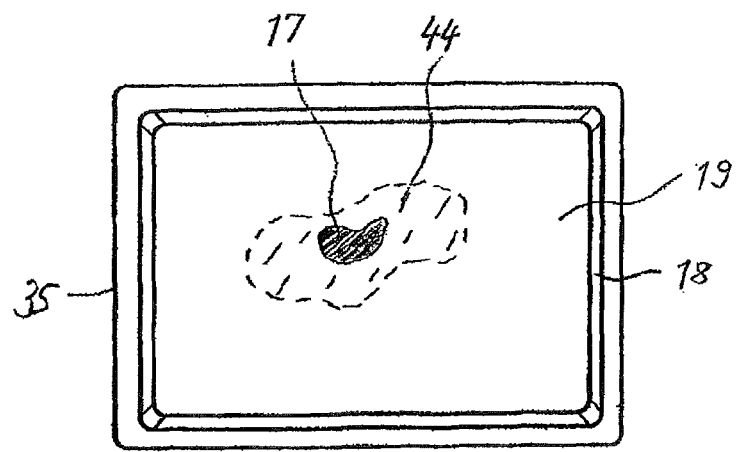
FIG. 9 is a plan view thereof.
Figure 10:
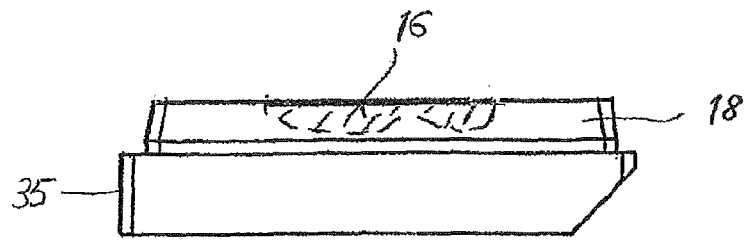
FIG. 10 shows a precut sample having a maximum cross-sectional area.
Figure 11:
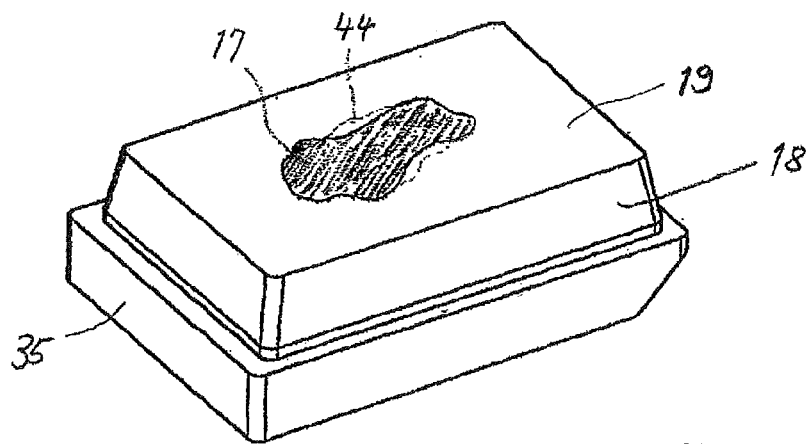
FIG. 11 is a perspective view thereof.
Figure 12:
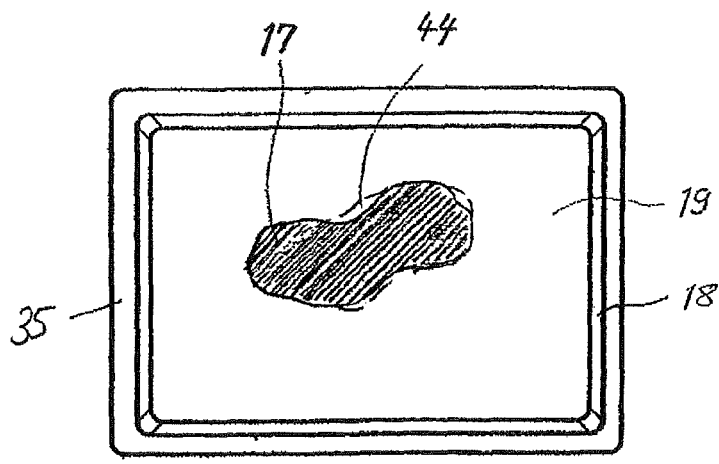
FIG. 12 is a plan view thereof.

FIGS. 10 to 12 depict, from various perspectives, paraffin block 18 in which a precut sample 16 is embedded; in contrast to FIGS. 7 to 9, sectioned area 17 of the precut sample 16 is equal to almost 100% of maximum cross-sectional area 44 of sample 16 in the section direction. In this case a suitable trimming plane is identified, since the relative trimming depth is greater than 80%.

Figure 13:
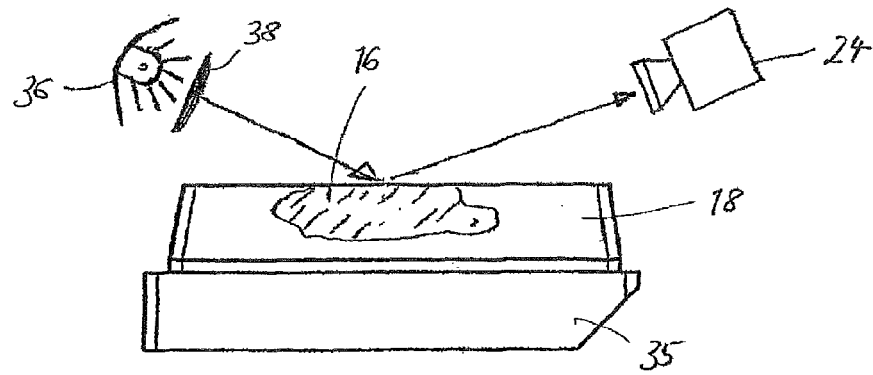
FIG. 13 shows an arrangement having a cassette, light source, and camera.
Figure 14:
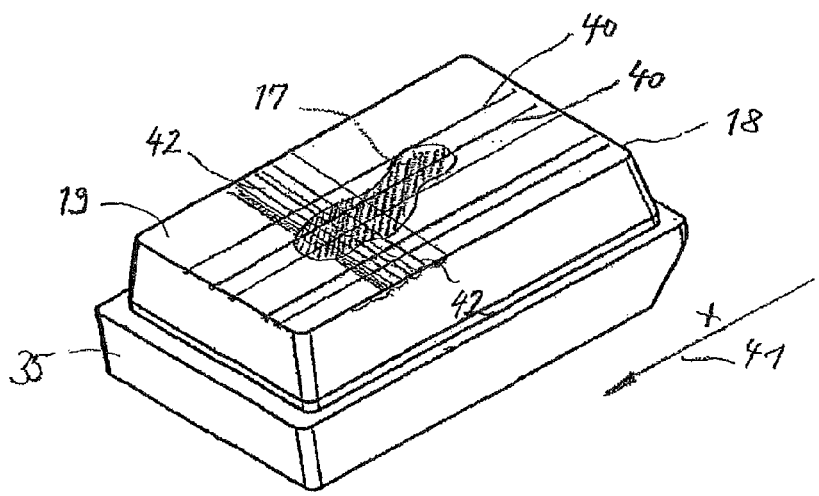
FIG. 14 is a perspective view of a cassette having a section that encompasses transverse and longitudinal grooves.
Figure 15:
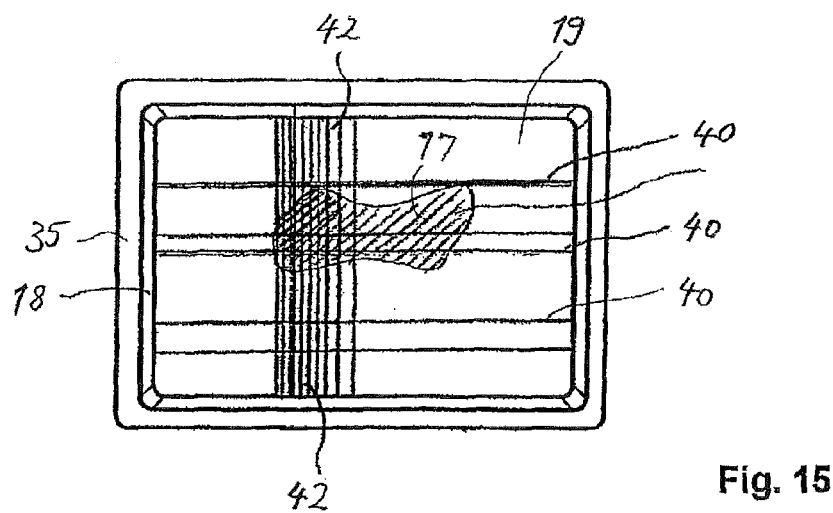
FIG. 15 is a plan view of the arrangement according to FIG. 14.

FIGS. 13 to 15 describe in further detail the procedure for image-based sensing in order to determine the number and width of the longitudinal striations as a characteristic value for thin-section quality, and the number and width of the transverse grooves as a characteristic value for thin-section quality.

FIG. 13 shows, in a simplified sectional depiction a side view of paraffin block 18 that is arranged on cassette 35. Sample 16 to be sectioned, for example a specimen of biological tissue material, is embedded in this paraffin block 18. Camera 24, as well as the light, directed onto sectioned area 17 of sample 16, of a light source 36, serve for image-based sensing of surface 19 of paraffin block 18 and of sample sectioned area 17, the light source encompassing a color filter apparatus or polarizing filter apparatus 38. A fluorescence device, in which the fluorescent radiation emitted from the sample after corresponding excitation by the light of light source 36 is evaluated, can also be included. Light having a specific wavelength or polarization can thus be generated by the use of the color filter apparatus, fluorescence filter, or polarization apparatus 38. Selection of the appropriate filter apparatus 38 depends on the tissue type of sample 16. Illumination by means of light source 36, and/or sensing of the image of sample 16, can each be accomplished at different angles in the range from 0° (vertical) to almost 90° (very flat).

FIG. 14 shows, in a three-dimensional depiction, paraffin block 18 having the embedded precut sample 16, surface 19 of paraffin block 18 and sectioned area 17 of sample 16 having longitudinal striations 40 along the cutting direction in the direction of X arrow 41, and simultaneously containing transverse grooves 42 transversely to the cutting direction. Longitudinal striations 40 are caused by a possibly damaged or blunt sectioning knife 14, whereas transverse grooves 42 originate from oscillating movements of the sectioning knife transversely to the cutting direction.

FIG. 15 shows, in a sectioned depiction, a plan view of paraffin block 18 with sectioned area 17 of the embedded sample 16. With the aid of camera 24 and an evaluation device 26 (not depicted here) coupled thereto, the quality of the thin sections can be identified by evaluating the images of sectioned area 17 of sample 16 in terms of predefined characteristic values for thin-section quality. With the aid of evaluation device 26, for example, the number of longitudinal striations 40 and/or the number of transverse grooves 42 on sectioned area 17 of sample 16 can be identified.

Figure 16:
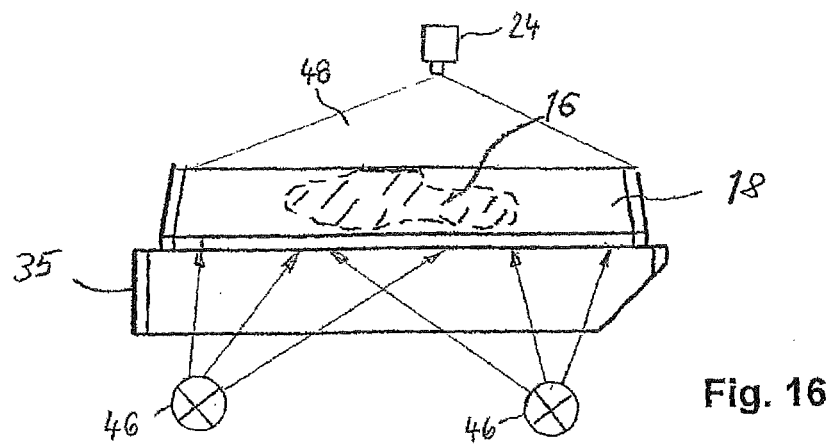
FIG. 16 shows an arrangement for identifying the maximum cross-sectional area of the sample.
Figure 17:
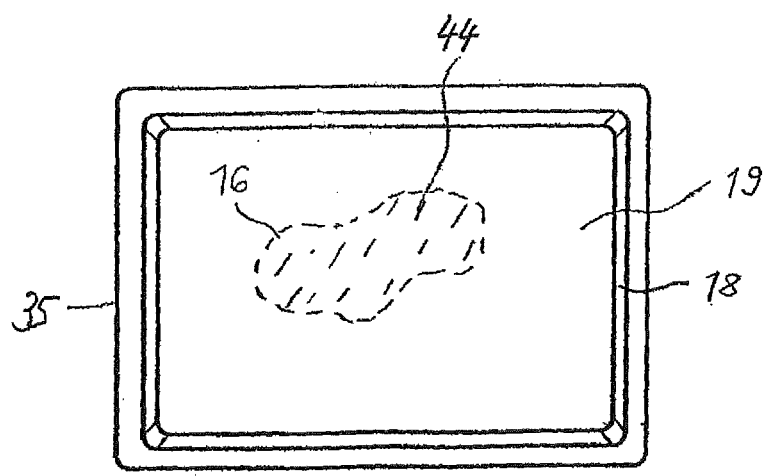
FIG. 17 is a plan view of the arrangement according to FIG. 16.
Figure 18:
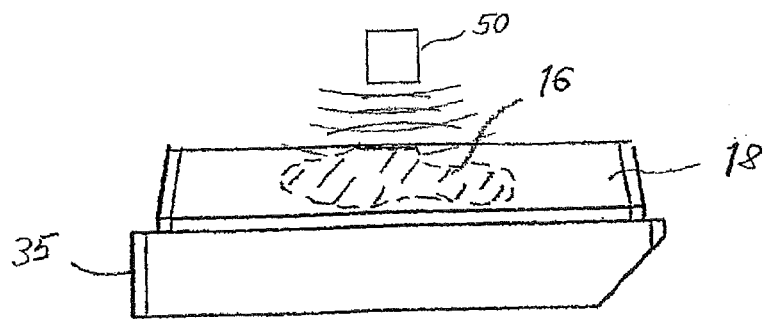
FIG. 18 shows an arrangement having an ultrasonic sensor.

FIGS. 16 to 18 show examples of the method step, discussed earlier, of sensing maximum cross-sectional area 44 of sample 16. In the example according to FIG. 16, cassette 35 is irradiated from the underside with light, e.g. from LEDs 46. Light sources of this kind can be arranged, for example, in microtome 10 in a receiving apparatus that receives cassette 35. Sample 16, embedded in paraffin block 18 and not yet precut, is accordingly illuminated from behind in a transmitted-light mode. Sample 16 has different transmission characteristics from the paraffin, so that a shadow image of the sample is presented to camera 24 within its sensing region 48. The area of this shadow image corresponds to the maximum cross-sectional area of the sample, as depicted in FIG. 17 as a plan-view image. It is also possible to illuminate the paraffin-embedded sample 16 from above, in incident-light mode, from camera 24. As a result of the differing reflection characteristics of sample 16 and paraffin, once again the area of sample 16 enclosed by the outline is detectable, and maximum cross-sectional area 44 can be identified. In a further variant according to FIG. 18, the embedded sample 16 is impinged upon on the front side (or also the back side) by ultrasound from ultrasonic sensors 50, and the maximum size and therefore maximum cross-sectional area 44 of the sample can be identified based on the ultrasonic radiation reflected from sample 16.

The method that has been presented can operate in partly automatic fashion, in such a way that a user is shown by the evaluation device, as an aid to his or her manual assessment, the assessment issued by the evaluation device for the section that has been made. In this fashion the user is assisted and supported by the above-described method in the assessment of sections from a large number of samples, thus enabling overall improved quality in the production of thin sections of a sample by means of a microtome. When the method is operating reliably, it is also possible to switch over to fully automatic operation, in which the assessment of section quality is performed solely by the evaluation device. The user would then be responsible only for loading and servicing multiple devices, the sectioning process proceeding automatically.

The method described creates uniform quality criteria for the assessment of section quality. These quality criteria are independent of the operator's state of mind, and of environmental conditions and other interfering influences. The method makes possible ideal adaptation to individual laboratory standards. Even operators who are not highly qualified can be trained quickly, and with the aid of the teach-in phase can acquire sufficient experience in the assessment of section quality. If a database already filled with data is used, an operator with little experience can operate the microtome, using the method described, without a great deal of training time.

LIST OF COMPONENT PARTS

10 Microtome
12 Base bed
13 Sectioning knife holder
14 Sectioning knife
16 Sample
17 Sectioned area of sample
18 Paraffin block
19 Surface of paraffin
20 Displacement path
22 Close-in region
24 Camera
26 Evaluation device
28 Operating console
30 Central control unit
31 Display apparatus
32 Data acquisition system
34 Image processing program
35 Cassette
36 Light source
38 Filter apparatus
40 Longitudinal striations
41 Direction of X arrow
42 Transverse grooves
44 Maximum cross-sectional area of sample
46 LEDs
48 Sensing region
50 Ultrasonic sensor

The invention claimed is:

1. A method for producing thin sections of a sample by cutting the thin sections from the sample by a microtome, comprising:
   repeatedly cutting in a teach-in phase the sample for generating a plurality of thin sections and corresponding sample cutting surfaces on the sample;
   acquiring in the teach-in phase by a camera images of said corresponding sample cutting surface on the sample;
   evaluating in the teach-in phase subjectively by a user whether the quality of the thin sections are good or poor and correlating the respective images of the sample cutting surfaces to the respective thin sections evaluated good or poor;
   determining in the teach-in phase by an image processing program characteristic values of the images of the sample cutting surfaces acquired by the camera and correlating these characteristic values to the respective thin sections evaluated good or poor for identifying correlating limit values for those characteristic values correlating to sufficiently good section quality;
   storing the limit values in an evaluation device; and automatically evaluating in a thin section production phase images of the sample cutting surfaces by the evaluation device for determining the characteristic values of the sample cutting surfaces and comparing these to the limit values to determine whether the respective thin sections of the sample are accepted or not accepted.

2. The method according to claim 1, further comprising determining a trimming plane in a trimming mode, wherein the section thickness for the section in trimming mode is in the range from 10 to 50 µm, preferably 20 to 30 µm.

3. The method according to claim 2, further comprising evaluating the contrast difference between a bright surface of a paraffin block in which the sample is embedded, and a dark sectioned area of the precut sample that represents sample material, as a characteristic value by the evaluation device for determining the trimming plane.

4. The method according to claim 3, further comprising identifying the trimming plane when the sectioned area of a precut sample is equal to a predetermined portion of the maximum cross-sectional area in the section direction of the sample, preferably equal to at least 80%.

5. The method according to claim 1, further comprising selecting a section thickness in the range from 1 to 10 µm, preferably 2 to 5 µm, in a thin-section mode for producing thin sections, and setting a sectioning speed that is applied during sectioning to a reduced sectioning speed as compared to a sectioning speed in the trimming mode.

6. The method according to claim 5, further comprising setting the sectioning speed in the thin-section mode for producing the thin sections only after identification of the trimming plane.

7. The method according to claim 1, further comprising selecting the number of longitudinal striations on the sample cutting surface for each thin section along the cutting direction as a characteristic value for thin-section quality, and accepting the relevant thin section if the number of striations is below a predetermined value, preferably below five.

8. The method according to claim 1, further comprising selecting the number of transverse grooves on the sample cutting surface for each thin section transversely to the cutting direction as a characteristic value for thin-section quality, and accepting the relevant thin section if the number of transverse grooves is below a predetermined value, preferably below five.

9. The method according to claim 1, further comprising indicating to a user whether the current thin section is accepted or not accepted by means of a display apparatus.

10. The method according to claim 9, further comprising replacing a sectioning knife when a predetermined number of unaccepted successive thin sections is exceeded.

11. The method, according to claim 9, further comprising correcting sectioning parameters when a predetermined number of unaccepted successive thin sections is exceeded.

12. The method according to claim 11, further comprising modifying at least one of a sectioning speed, a relief angle and a section thickness in order to correct the sectioning parameters.

13. The method according to claim 1, further comprising continuing the sectioning process in a trimming mode once at least one of a) a predefined number of acceptable thin sections was created; b) a predefined number of unacceptable thin sections were created; and c) upon an operator instruction; and further comprising determining a new trimming plane and transitioning into a thin-section mode after execution of the aforementioned method steps.

14. The method according to claim 1, further comprising identifying the maximum cross-sectional area of the sample in a transmitted-light mode on an uncut sample by one of a camera and an ultrasonic measuring method.

* * * * *